United States Patent [19]

Gerow

[11] Patent Number: 4,623,116

[45] Date of Patent: Nov. 18, 1986

[54] APPARATUS FOR PROTECTING A PRE-FORMED PROJECTING APPENDAGE DURING PLASTIC MOLDING

[75] Inventor: Frank J. Gerow, Houston, Tex.

[73] Assignee: Synergist Limited, Houston, Tex.

[21] Appl. No.: 654,782

[22] Filed: Sep. 26, 1984

[51] Int. Cl.[4] .................... B29C 39/02; B29C 45/03
[52] U.S. Cl. ....................................... 249/55; 249/83;
249/93; 249/122; 249/142; 249/144; 249/178;
425/116; 425/127; 425/542; 425/469
[58] Field of Search ................ 249/122, 142, 149, 83,
249/175, 177, 55; 425/110, 116, 117, 127, 129
R, 457, 469, 472, 542, 543

[56] References Cited

U.S. PATENT DOCUMENTS

| | | | |
|---|---|---|---|
| 2,330,399 | 9/1943 | Winder | 264/305 |
| 2,443,630 | 6/1936 | Raiche | 264/305 |
| 3,031,720 | 5/1962 | Rempel et al. | 264/278 |
| 3,287,483 | 11/1966 | Morin | 264/275 |
| 3,328,846 | 7/1967 | Morin | 264/275 |
| 3,484,516 | 12/1969 | Simons | 264/275 |
| 3,761,557 | 9/1973 | Werner | 425/110 |
| 3,887,323 | 6/1975 | Bratten | 425/517 |
| 3,898,121 | 8/1975 | Holyroyd | 156/500 |
| 3,901,965 | 8/1975 | Honeyman | 264/328 |
| 3,919,374 | 11/1975 | Komendowski | 264/278 |
| 3,991,146 | 11/1976 | Barrie | 264/46.7 |
| 4,210,478 | 7/1980 | Shoney | 156/142 |
| 4,284,459 | 8/1981 | Patel et al. | 156/245 |

Primary Examiner—Willard E. Hoag
Attorney, Agent, or Firm—Darryl M. Springs

[57] ABSTRACT

Apparatus are disclosed for injection molding a generally cylindrical sleeve-like penile prosthesis from a thermoplastic or thermosetting material utilizing a male mold core and a pair of female mold halves in which the molded prosthesis has encased in a wall therein a portion of a pre-formed length of resilient tubing, the remaining length and free end of the tubing extending from the molded prosthesis as a length of free tubing projecting therefrom. The apparatus includes a mandrel for carrying the mold core and is adapted for mounting between the female mold halves, and means for anchoring one end of the preformed tubing at a selected position on the mold core. The apparatus further includes a first portion of the tubing after the anchored one end positioned adjacent at least a portion of the mold core, a box-like member on the mandrel and positionable adjacent the mold core surface for accepting and isolating the remaining length and free end of the tubing extending past a predetermined location for the tubing to exit the molded prosthesis.

19 Claims, 16 Drawing Figures

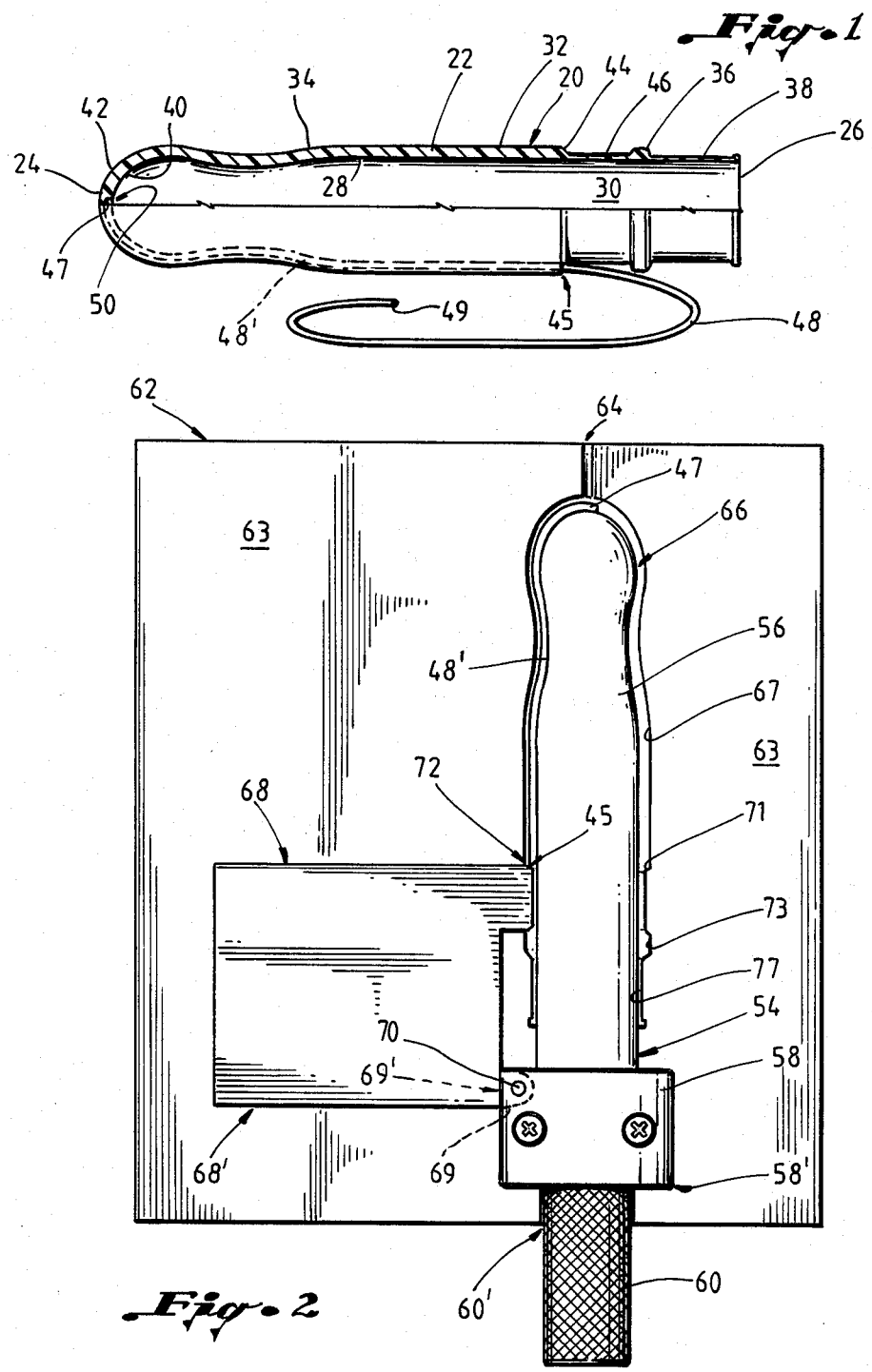

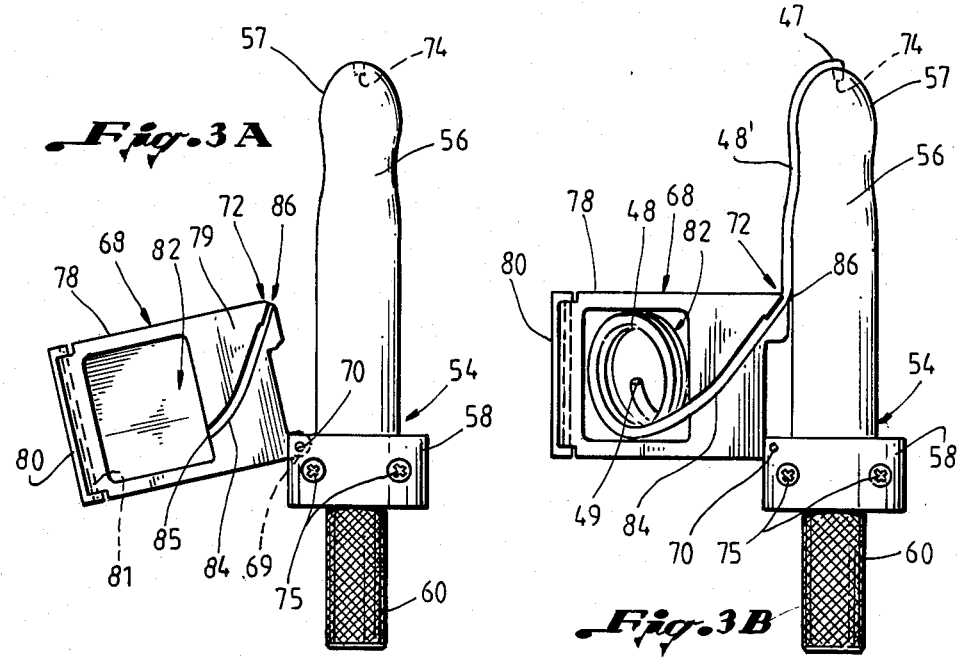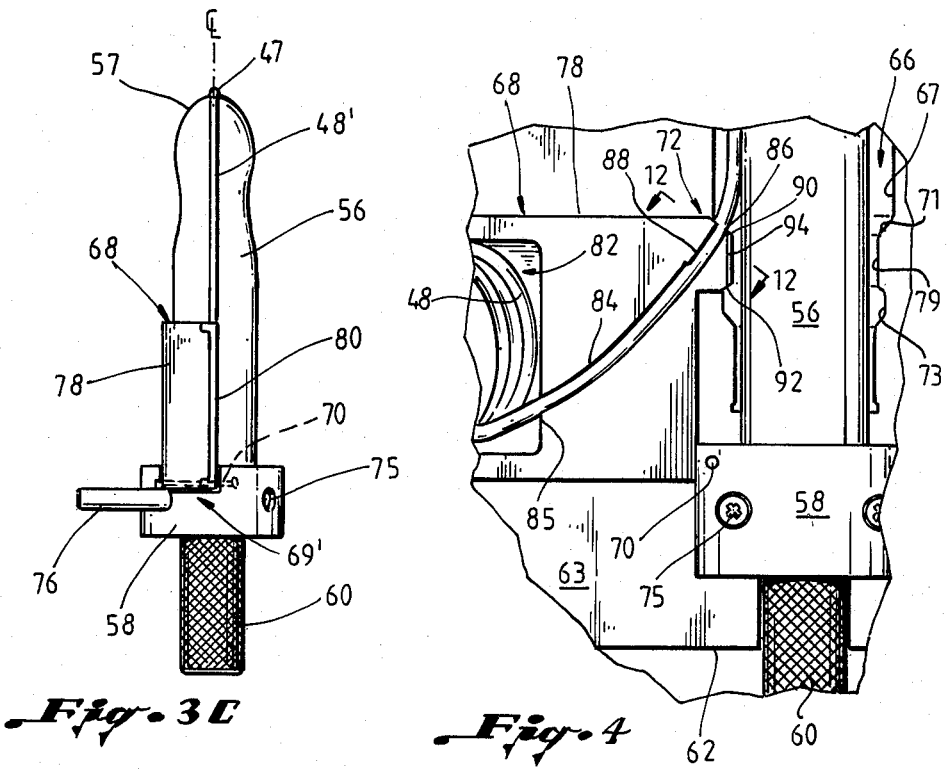

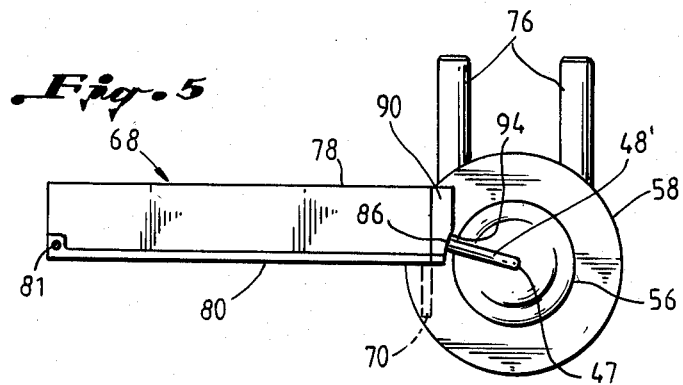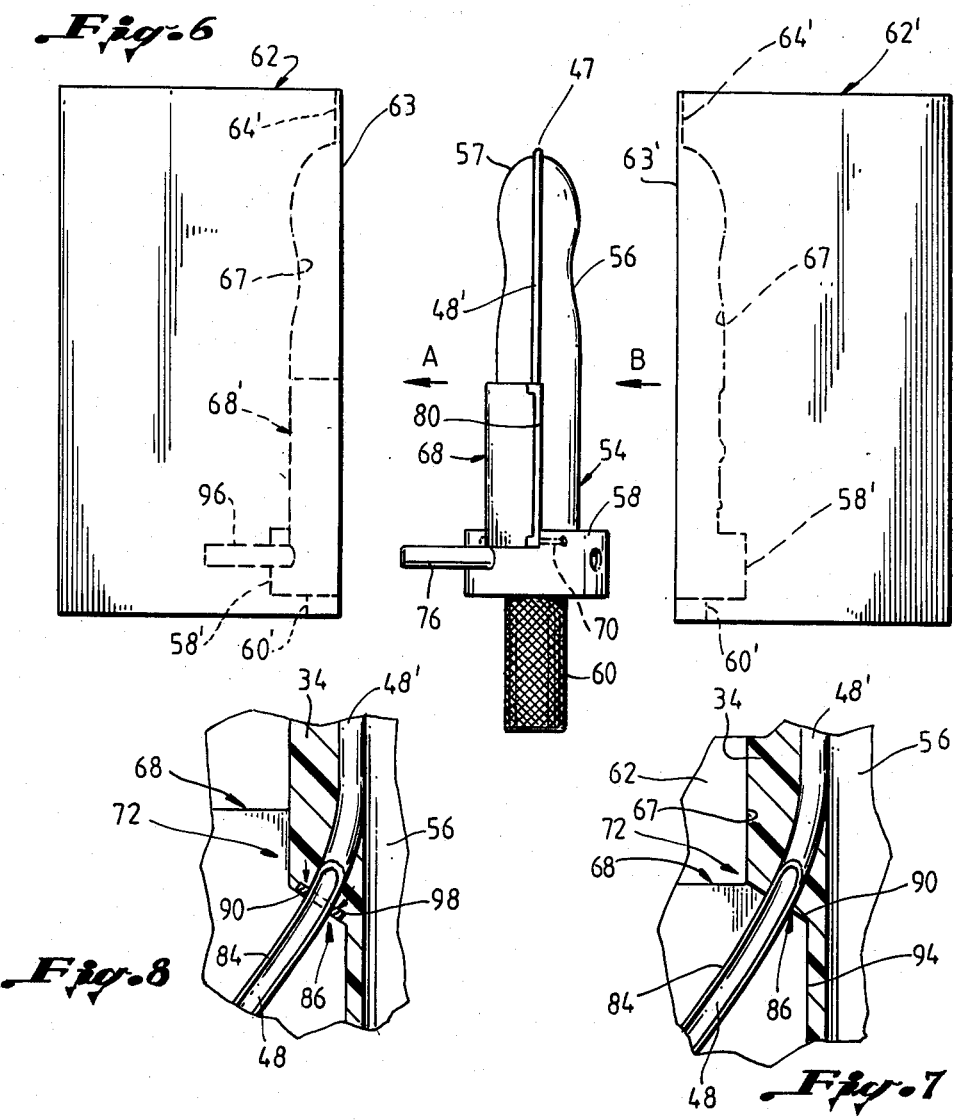

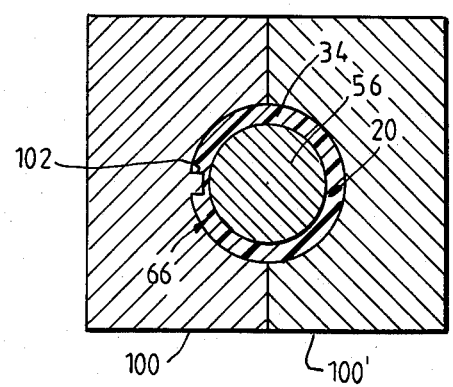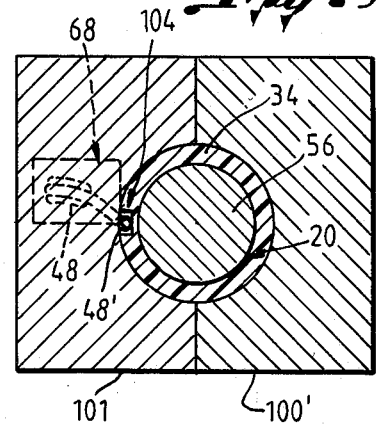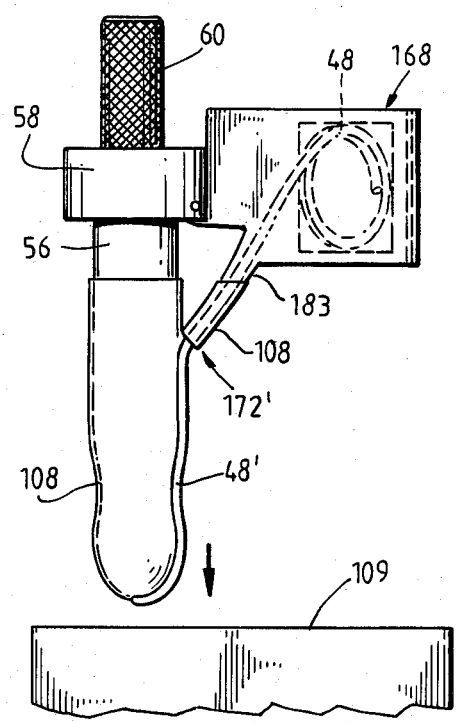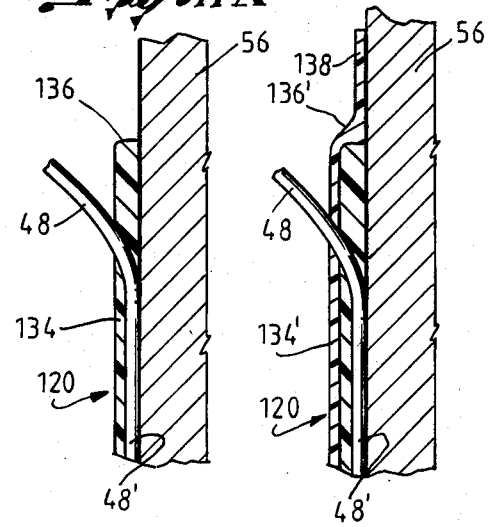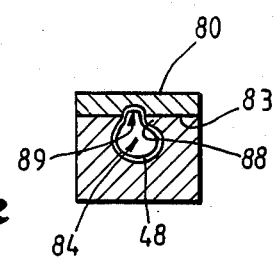

APPARATUS FOR PROTECTING A PRE-FORMED PROJECTING APPENDAGE DURING PLASTIC MOLDING

DESCRIPTION

BACKGROUND OF THE INVENTION

This invention relates to molding products of thermoplastic or thermosetting plastic materials and particularly to products having molded therein a portion of a pre-formed elongated member or component with the remaining length and free end of the pre-formed elongated component extending from the molded product to form a projecting elongated appendage that is not imbedded or covered with the plastic material.

In forming many molded products, particularly in using an injection molding process, it is often desirable or necessary to provide a length of a pre-formed component or member, such as a tubing, wire, ribbon, rod or pin, or the like, for partial imbedding in the molded product. It is necessary to prevent the remaining length of the pre-formed component from being coated by or imbedded in the plastic material and to protect the pre-formed member projecting therefrom from being damaged during the molding process.

The prior art discloses other methods and apparatus for preventing the remaining length of the pre-formed member from being coated by or imbedded in the plastic material but does not consistently protect the pre-formed component from damage during the molding process or while the molded product is later removed from the mold. In injection molding, the prior art makes use of a groove or channel in one face of a female mold half to carry the remaining length and free end of the pre-formed member from the mold cavity to the exterior of the mold, or uses an aperture through a female mold half communicating with the mold cavity and the exterior of the mold.

In the former case, the use of a groove in the mold face, problems arise in the proper alignment of the pre-formed member, such as a flexible tubing, wire, ribbon or a rod pin, within the groove during the closing action of the mold. If the pre-formed member is not exactly aligned in the groove when the mold halves close, the high closing pressure during the molding process will damage the member and cause a reject and loss of product. In addition, extrusion of the molding material can occur along the groove around the pre-formed member and then cure around the member which will also cause a reject and loss of the product.

In the latter case, the use of an aperture through the mold body prevents the problem of "pinching" or damage to the pre-formed member during the mold closing action. However, the pre-formed member is often hard to extract from the aperture or port after the product is molded, often resulting in damage to the pre-formed member or the product upon removal, and again resulting in loss of product and wasted time in attempting to remove the molded product and it projecting elongated appendage from the mold.

When using flexible or compressable pre-formed members, such as tubing or the like, the fixed size of the aperature or port may not prevent extrusion of the molding material through the aperature around the preformed member. If this happens, then the extruded material will cure around the pre-formed member which will again cause rejection and loss of the product. In addition, extrusion of the material into the aperture or port may also make it difficult to remove the molded product from the mold. On the other hand, if the aperature or port for receiving the pre-formed member through the mold half is made smaller to reduce the extrusion problem, then it may be next to impossible to feed the pre-formed member, particularly if it is constructed of a flexible and compressible material like a flexible tubing, rope, line or the like, into and through the aperature in the mold half to begin with. In other molding processes, similar problems are presented in protecting the projecting elongated appendage from plastic coating and from damage during the molding process.

The inventor herein has previously obtained a patent, U.S. Pat. No. 4,175,554, on a prosthesis for receiving and positioning in a simulation of an erection the male penis for use by men who are sexually impotent. The prosthesis can be described generally as a penile-shaped, sleeve-like, smooth walled, elastic, relatively soft and pliable hollow cylindrical body with a closed distal end and an opposing open proximal end. A flexible, small-diameter tubing, having an outer diameter less than the wall thickness of the body has a portion thereof encased or embedded in the wall of the prosthesis, with one encased end communicating with the interior of the prosthesis at its most distal end. The tubing exits the wall of the prosthesis toward the proximal end and the remaining length and free end are used in mounting the prosthesis by the patient.

Because of all of the problems above described, the inventor found a unanimous opinion in the plastic molding industry that the prosthesis with its projecting elongated tubing could not be successfully and commercially mass-produced, using current molding technology, but it would have to be hand-made one at a time on a core by a "layering" process. The limitations and disadvantages of the prior art have been successfully overcome with the present invention, and the prosthesis, or any other plastic molded product having a projecting pre-formed member, can now successfully be mass-produced using modern injection molding or dip molding processes.

BRIEF SUMMARY OF THE INVENTION

In accordance with the present invention, methods and apparatus are provided for molding a product from a thermoplastic or thermosetting plastic material in which the product has imbedded therein a portion of a pre-formed elongated member, the remaining length and free end of the pre-formed member being isolated and protected during the molding process in order to form an elongated appendage projecting from the molded product that is free of the molding material.

In a preferred embodiment where the molded product is a generally sleeve-shaped, smooth walled, hollow cylindrical penile prosthesis formed by an injection molding process, the prosthesis is formed over a mold core mounted on a mandrel and adopted to be matingly engaged between a pair of female mold halves. Each female mold half has a machined cavity that cooperates and mates with the male mold core for forming the penile-shaped cavity for molding the prosthesis. The lower part of the mandrel includes an enlarged alignment head and a handle for removing the mandrel from the mold. A flexible plastic or rubber tubing has one end anchored to the extending end of the mold core, and a first portion of the tubing is positioned downwardly over the surface of the mold core.

A box-like storage means is mounted on the mandrel for accepting and isolating the remaining length and free end of the tubing extending past a predetermined location for the tubing to exit the molded prosthesis, and for storing and protecting the remaining length and free end of the tubing during the molding process. The box-like storage means snugly fits into a mating machined box-like cavity disposed in the face of one of the female mold halves adjacent said mold core and female mold cavity during the injection molding process.

The storage means includes a gate section positionable adjacent the mold core surface for accepting and isolating the remaining length of the tubing extending past the predetermined location for the tubing to exit the molded prosthesis. The storage means also includes a box-like member having a storage cavity therein communicating with the gate section for receiving and storing the remaining length and free end of the tubing, and a lid for covering and sealing the box-like member for protecting the tubing length stored in the cavity during the molding process.

The gate section comprises a defined mold surface of the box-like member cooperating with the mold core surface and one of the female mold half molding surfaces for defining at least a portion of the surface of the molded product, and more particularly, at least the surface contour of the exit location of the tubing from the molded prosthesis. The box-like member is mounted on the mandrel and adopted for limited arcuate movement toward or away from the mold core to permit the gate section of the defined mold surface to be positioned into a closely spaced relationship with said mold core surface.

The tubing is anchored and positioned on the mold core and the box-like member is positioned to place the gate section surfaces thereof in a proper position adjacent the mold core surface to define the surface contour of the prosthesis where the tubing will exit. The tubing extending past the exit location is inserted in an aperture in the gate section and into a chamnnel in the face of the box-like member to direct the remaining length and free end of the tubing into the storage cavity. The receiving aperture in the gate section surface fits the tubing snugly to prevent leakage of the injected liquid molding material during the injection molding process.

The lid is closed to seal the storage means for protecting the tubing. The mandrel and mold core with attached tubing and storage means is placed into one female mold half that receives the mold core and the box-like storage means into a box-like mating cavity in the mold half. The storage means fits tightly into the receiving cavity in the mold half and the lid of the storage means fits flush with the outer mating surface of the female mold half. This permits pressure to force the two female mold halves together to mate and seal the mold halves into a unitary mold and to seal and retain the tubing storage means with the female mold halves during the molding process.

After the liquid plastic material is injected into the mold and cures, the female mold halves are parted, and the mandrel with formed penile prosthesis on the mold core and the mounted tubing storage means are removed. The lid of the storage means is opened, the stored tubing length is freed from the storage cavity, the channel and gate section and the molded prosthesis is then removed. The remaining length and free end of the tubing then forms an elongated appendage projecting from the molded prosthesis body.

While the above method and apparatus were described with particular reference to an injection molding process, the mandrel with mold core and mounted storage means could be adopted for molding the prosthesis or other product using a dip molding process. The storage means functions to store and protect the free end and remaining length of the tubing during the dip molding process.

The present invention has a primary feature of isolating and protecting the remaining length and free end of a pre-formed member during the molding process by a storage means that is mounted on the mold mandrel.

Another primary feature of the present invention as it applies to injection molding is that the means for storing the remaining length of any pre-formed member to be partially encased in the molded product is located within the female mold halves adjacent to and mounted on the mold core to eliminate damage to the pre-formed member during mold closing or upon removal after the product is cast.

BRIEF DESCRIPTION OF THE DRAWINGS

In order that the manner in which the above-recited advantages and features of the invention are achieved can be understood in detail, a more particular description of the invention will now be made by reference to specific embodiments thereof which are illustrated in the accompanying drawings, which drawings form a part of this specification.

In the drawings:

FIG. 1 is a side view in elevation, partially cut-away, of the prosthesis intended to be manufactured by the instant invention.

FIG. 2 is a front view in elevation of a female mold half with the male mold portion and mandrel in place according to the present invention.

FIG. 3A is a front view in elevation of the mold core with the attached tubing storage means shown with its lid in an open position.

FIG. 3B is a front view in elevation of the mold core mandrel with a plastic tubing in place, and the excess tubing stored in the tubing storage means.

FIG. 3C is a side view in elevation of the mold core mandrel, and the attached tubing storage means with its lid in a closed position.

FIG. 4 is an enlarged fragmentary front view of a female mold half, the mandrel and mold core and the tubing storage means showing the cooperative interface between the mold core, tubing, the female mold half, and the and gate section of the storage means.

FIG. 5 is a top plan view of the mandrel and attached tubing storage means.

FIG. 6 is a side view in elevation showing the relationship between the two female mold halves and the mandrel with attached tubing storage means.

FIG. 7 is an enlarged fragmentary view of the cooperative interface between the mold core surface, the tubing and the gate section surfaces.

FIG. 8 is an enlarged fragmentary view of the cooperative interface between the mold core surface, the tubing and the gate section surfaces showing an embodiment for preventing leakage of the molding material into the tubing storage means.

FIG. 9A is a horizontal cross-sectional view of a second embodiment of the present invention showing the configuration of one of the female mold halves for the first injection molding step.

FIG. 9B is a horizontal cross-sectional view of a second embodiment of the present invention showing the altered configuration of one of the female mold halves for the second injection molding step.

FIG. 10 is a front view in elevation of a mold mandrel and attached modified tubing storage means as may be utilized in a dip-molding process.

FIG. 11A is a fragmentary, vertical cross-sectional view of a mandrel carrying an injection molded product in a partial stage of completion.

FIG. 11B is a fragmentary, vertical cross-sectional view of a mandrel carrying the injection molded product shown in FIG. 11A with a completed outer dip-molded layer of plastic material that forms a separate portion of the completed product.

FIG. 12 is a cross-sectional view of the tubing storage means with closed lid taken along lines 12—12 of FIG. 2.

DETAILED DESCRIPTION OF THE INVENTION

Referring to FIG. 1, a molded product 20 made in accordance with the present invention is shown. Product 20, in the description which follows, will be described in detail as a penile prothesis; however, the molded product 20 can be any product adapted for molding from a thermoplastic or thermosetting material that has partially molded therein at least a portion of a pre-formed elongated member, a remaining length and free-end of the elongated member projecting from the molded product as an elongated appendage.

The molded prosthesis 20 comprises a generally penile-shaped, sleeve-like, smooth walled, elastic, relatively soft and pliable hollow cylindrical body 22 with a closed distal end 24 and with an opposing open proximal end 26. An inner surface 28 defines a generally cylindrical chamber 30 extending from distal end 24 lengthwise through body portion 22 to communicate with the open proximal end 26. Prothesis 20 is formed with a relatively thick-wall section 34 between inner surface 28 and outer surface 32. Thick-wall section 34 extends from the most distal end 24 to an annular shoulder 44 that tapers to a somewhat thinner wall section 46 terminating in a thicker annular rib portion 36, which is spaced from the proximal open end 26. However, the prosthesis 20 could have a body 10 having a thick-wall section 34 extending from distal end 24 to the annular rib 36.

The portion of body 10 extending from the annular rib portion 36 to the proximal end 26 is a relatively thin-walled portion or section 38. In a finished product, actual prosthesis 20 may have a thick-walled body section 34 having a thickness ranging from 0.05 to 0.10 inches, with the thin-walled section 38 having a thickness ranging from 0.005 to 0.010 inches, thus forming an extremely thin flexible end. The distal end 24 includes rounded inner and outer surfaces 40 and 42, respectively, with the same or slightly thinner wall thickness as wall section 34.

A flexible, small-diameter tubing 48, having an outer diameter less than the thickness of the thick-walled section 34, has a portion 48' molded or imbeded in the thick-wall section 34 with an extending portion terminating in a free end 49. The end 47 of the tubing 48' molded in the wall section 34 of prosthesis 20 communicates with the interior chamber 30 at the most distal end portion of the interior rounded surface 40 through a duct or port 50. The imbedded portion 48' of tube 48 exits the prosthesis body 22 at the annular shoulder 44 at a location 45 and comprises a free length of tubing 48 exterior to the prosthesis 20 and terminates in a free end 49.

The preferred molding material has been found to be an organo silicone elastomer of one of the many configurations of such elastomers. The preferred elastomer is a dimethyl polysiloxane or a polysiloxane containing vinyl or other similar elastomers of that grouping. The flexible tubing 48 is preferably formed of any suitable elastomer product, but when the polysiloxane elastomers above are used for the body of the prosthesis, it has been found advantageous to use platinum catalyst organo silicone elastomers because of their superior bonding characteristics. Of course, any suitable material can be used if it is flexible and elastic, such as polyurethane and polyvinyl. Any suitable material may be used in constructing the prosthesis and the tubing as long as the basic requirements as to elasticity, relative softness and pliability are met.

In the broadest sense, prosthesis 20 forms a molded product formed of a thermoplastic or thermosetting material that has a pre-formed elongated member 48, having a portion thereof 48' partially molded therein, and a free remaining length 48 and free end 49 forming and elongated, flexible appendage projecting from the molded product 20. The instant invention discloses a unique and successful process and apparatus for molding such a plastic product with a projecting elongated flexible appendage without damaging the projecting flexible appendage during the molding process.

Referring now to FIG. 2, a plastic injection molding apparatus for molding prosthesis 20 is shown. A female mold half 62 having a face 63 for mating with a second female mold half (not shown) is provided having a mold cavity surface 67 therein for cooperatively mating with the mold core 56 portion of the mandrel 54. The cavity 67 cooperates with the mold core 56 to form a product mold cavity 66 for forming the prosthesis 20 as earlier described. An injection port or sprue 64 is provided for injecting the liquid molding material into the interior of the mold 62.

The female mold half has a fitted cavity 58 for receiving the alignment head 58' portion of mandrel 54 and an opening 60' for accommodating the gripping handle 60 of mandrel 54. The female mold half 62 also has disposed therein in cooperation with the surface of cavity 67 an annular shoulder 71 for forming the radial shoulder 44 of prosthesis 20, an annular channel 73 for forming the annular rib portion 36 of prosthesis 20, and a surface 77 for forming the thin sleeve-like portion 38 of prosthesis 20.

The female mold half 62 has disposed in its face 63 a generally rectangular cavity 68' for accommodating a storage means 68 as will hereafter be described in greater detail. The storage means 68 also includes a gate section 72 that will be hereafter further described. The storage means 68 is mounted on mandrel 54 by means of a projecting flange or lug 69 adapted for mating with a slot 69' disposed in the alignment guide 58 portion of mandrel 54 and is secured therein by means of a pin 70.

Storage means 68 is capable of limited arcuate movement in a vertical plane toward and away from mold core 56 to position the gate section 72 in a closely spaced relationship to the surface of mold core 56 for cooperating therewith to define at least a portion of the surface of the molded prosthesis as appears between annular ridge 44 and annular ring 36. The gate section 72 also defines the exit location 45 of the first portion 48' of the tubing from the molded prosthesis 20.

Referring now to FIGS. 2–6, the method and apparatus according to this invention will now be described in greater detail. In FIGS. 3A–C, a mold mandrel 54 is shown, including a generally cylindrical male mold core 56 portion having a shaped end portion 57, a mold alignment guide head 58 and a handle 60. Alignment pins 76 are secured in place by means of screws or bolts 75. The storage means 68 as hereinabove described comprises a box-like member 78 and the previously described gate section 72. The generally rectangular box-like member 78 has disposed therein a storage cavity 82. A lid 80, hinged to the box-like member 78 by means of a hinge pin 81, is shown in the open position. A channel 84 is provided in the face 79 of box-like member 78 and communicates with cavity 82 and an aperture 86 provided in one face of the gate section 72.

In FIG. 3A, the storage means 68 is shown with the lid 80 in the open position for providing access to the interior of the storage means. The box-like storage means is mounted on the mandrel 54 by means of a projectng lug or ear 69 (housing an aperature disposed therethrough) which is inserted in a slot 69' of the alignment head 58 (see FIG. 3C) and secured by means of a pin or shaft 70. The shaft 70 permits limited vertical arcuate movement in a vertical plane of the storage means 68 toward or away from the mold core 56 to position the gate section 72 as previously described. In FIG. 3A, the storage means 68 and gate section 72 are shown in their "down" or "disengaged" position relative to the surface of mold core 56.

In FIG. 3B, a length of flexible tubing 48 has been anchored at one end 47 in a shallow attachment port 74 at the extreme extending tip of the penile prosthesis mold core 56. A first portion of the tubing 48' has been positioned over the surface of the mold core 56 down to a predetermined location 45 fixed by the gate section 72 of storage means 68 that has been rotated to its "up" or "engaged" position relative to the surface of the mold core 56. The remaining length of tubing and free end 49 are inserted through the gate aperture 86 and threaded through channel 84 and aperture 85 into the storage cavity 82. The remaining length of tubing 48 and the free end 49 are coiled in the cavity 82 for storage.

As may be seen in greater detail in FIGS. 4, 5 and 7, the gate section 72 of the box-like member 78 has outer surfaces 90, 92 and 94 that cooperate with the surfaces of mold core 56 and the surfaces of mold cavity 67 to form the outer surface of the prosthesis 20 and define the exit location 45 of the tubing 48 from the molded prosthesis. The surface 90 of the gate section has a shoulder contour that coincides with the contour of the annular shoulder 71 in the mold cavity 67. The curved longitudinal surface 94, that is closely spaced parallel to the surface of mold core 56, corresponds to the contour and shape of the mold cavity surface 79 intermediate annular shoulders 71 and 73, which correspondingly forms the thinner section 46 of the prosthesis (see FIG. 1). Similarly, the slanted shoulder 92 of gate section 72 corresponds to the upper annular shoulder of the mold cavity annular channel 73.

Thus, it can be seen that the gate section 72 has defined mold surfaces 90, 92 and 94 that cooperate with the mold core 56 and the female mold cavity surface 67 to form a least a portion of the outer surface of the molded prosthesis, and, particularly, to locate and define the surface contour of the molded prosthesis at the exit point for the tubing 48. In addition, as can be seen in FIG. 4, the gate section 72 also provides an internal lip 88 that is adjacent the outer surface 90 and aperture 86 and partially covers or closes the width of channel 84. Lip 88 provides a means of "squeezing" the tubing 48 at the point it enters the gate aperture 86 to increase the sealing pressure at the surface 90 due to the internal resilience of the tubing 48. Lip 88 also "grips" the tubing at this point to prevent its "popping out" of aperture 86 while the remaining length and free end 49 of tubing 48 is coiled and stored in cavity 82. However, since the tubing 48 is resilient and elastic, it can easily be defeormed, without damage, to be manually inserted into and withdrawn from aperture 86 and channel 84 under lip 88.

Referring to FIGS. 4 and 12, the relationship of the lid 80 to the body member 78 and, in particular, gate section 72 is shown. The inner surface 83 of lid 80 is machined to effect a tight sealing fit with surface 79 of body member 78, and to close channel 84. However, in the open portion of channel 84 adjacent lip 88, lid 80 has a relief groove 89 disposed therein which corresponds to the length of lip 88. The relief groove 89 is provided in lid 80 to accommodate any "protruding" or "bulging" of tubing 48 that may occur alongside of lip 88 when the tubing 48 is compressed and defomed to fit into aperture 86 and under lip 88. The relief groove 89 will accommodate any "bulging" of tubing 48 and prevent pinching of the tubing between lid 80 and body member 78 that could damage the tubing at that point.

FIG. 6 discloses the relationships between injection molding female mold halves 62—62' and the male mold core 56 and mandrel 54 carrying the storage means 68 according to this invention. Referring to FIGS. 2 and 6, a pair of injection molding female mold halves 62 and 62' are shown in a spaced relationship as would be typical of the separation of the mold halves just prior to or just subsequent to the actual injection molding process.

The mold half 62 has an inner mold cavity surface 67 communicating with an injection sprue or port 64'. Mold half 62 also has a box-like cavity or recess 68' that cooperatively mates with the storage means 68 for inletting the storage means into the mold face 63 in order that the lid surface 80 of the storage means is flush with the outer mold face 63. Mold 62 has a pair of drilled apertures 96 for receiving the alignment pins 76 attached to the mandrel 54 and projecting from the rear of the enlarged alignment head 58. Mold half 62 has a mating cavity 58' for mating with the mandrel alignment head 58. The alignment head cavity 58' and the alignment pin apertures 96 are machined to an extremely close tolerance with the dimensions of the alignment head 58 and the guide pins 76 in order that the mandrel will precisely fit into mold half 62 and maintain the correct mold tolerances 66 (see FIG. 2) for each molded product. Mold half 62 also has an opening 60' in the lower face for accommodating the mandrel handle 60 and permitting its projection below the mold.

The other female mold half 62' carries similar mating cavities, such as cavity surface 67 for cooperatively mating with the mold core 56 to form the mold cavity for the product, alignment head cavity 58' for receiving the alignment head 58, and the opening 60' by accommodating the mandrel handle 60. Mold half 62' also carries a mating injection port of sprue 64'.

In an actual molding operation using the injection molding apparatus above described, the sequence of events would be as follows:

1. One end 47 of a pre-formed tubing 48 would be anchored in the extreme tip 74 of the mold core 56;
2. A first portion of the tubing 48 would be positioned along the surface of the mold core in a desired configuration;
3. The storage means 68 would be opened and rotated up to position the gate section 72 in cooperative spaced relation to the surface of mold core 56 to determine the location of the exit 45 of the rubber tubing 48 from the molded product;
4. The remaining tubing length 48 and free end 49 are inserted in the aperture 86 of the gate section 72 for isolating the tubing 48 from the product mold cavity 66 and directing the tubing to the storage cavity 82 for storage and protection;
5. The lid 80 would be closed on storage means 68 to seal the storage means, and the mandrel 54 with mold core 56 and mounted tubing and storage means 68 are moved in direction A to seat in the female mold half 62;
6. The female mold half 62' is then mated with mold half 62 to complete the product mold cavity 66 by moving mold half 62' in the direction B until mating sealing faces 63—63' of mold halves 62 and 62', respectively, are engaged and placed under pressure;
7. Liquid molding material is then injected into the interior product mold cavity 66 through sprue port 64 to form the molded product and envelope the first tubing portion 48' in the wall of the prosthesis 20;
8. Mold half 62' is removed from mating engagement with mold half 62 to release the mandrel 54 and permit removal of the mandrel and mold core with the molded product thereon from female mold half 62; and
9. Open the lid 80 of storage means 68 and free the remaining length 48 and free end 49 of the tubing from storage to form an elongated appendage 48 projecting from the molded prosthesis.

FIG. 8 discloses another sealing embodiment to seal the gate section aperture 86 interface with the pre-formed product or tubing 48'. In some circumstances, the resilient expansion pressure of the pre-formed member, such as an elastic, resilient and flexible tubing 48 will not consistently seal against the intrusion of the molding material into channel 84 through the interface of aperture 86 and tubing 48, because of higher injection pressures and thermal temperature expansion variations due to molding temperatures (see FIG. 7). A limited amount of leakage can sometimes occur but will generally form "flashing" that can easily be trimmed from the product.

A simple solution, however, is to use a flat disc 98 of a plastic or other compatible material that is inserted over the tubing portion 48' and against the gate section surface 90 to act as a seal between the tubing 48' and aperture 86. The sealing ring 98 will be self-energizing because of the pressure exerted by the injected material acting against the seal ring 98 to force it into engagement with tubing 48' and gate section surface 90 as shown by the arrows in FIG. 8.

FIGS. 9A and 9B disclose another embodiment of the injection molding process and appratus according to this invention. In FIG. 9A, two female mold halves 100—100 are shown in cross section in cooperative mating relationship with a mold core 56. The mold half 100 has a vertical rib 102 that projects into the product mold cavity 66 between the female mold halves 100—100' and the mold core 56. During a first molding step, the prosthesis 20 is injection molded to obtain the full thickness of body wall 34, but it will have a longitudinal channel 104 (see FIG. 9B) disposed therein as formed by rib 102.

The female mold half 100 is removed and a tubing 48' is disposed in the longitudinal channel 104 and positioned with relation to the prosthesis as earlier described for the previous embodiment. The excess tubing 48 would then be stored in storage means 68, identical to that as hereinabove described, and a different female mold half 101, minus the longitudinal projecting rib 102, will be used as shown in FIG. 9B.

The prosthesis is again injection molded as shown in FIG. 9B and the tubing 48' will be imbedded in the prosthesis wall 34 in the groove or channel 104. Then, when the mold halves 100'101' are opened and the mold core 56 with molded prosthesis 20 is removed, the excess tubing 48 can be freed from the storage means 68 in the identical manner as hereinabove discussed.

FIG. 10 discloses a dip-molding apparatus to mold the prosthesis 20. The mold core 56, head 58 and handle 60 are identical to the mandrel 54 hereinabove described. However, the storage means 168 has been modified to provide a narrow extending neck 183 connecting the gate section 172 to the box-like storage means 168. The function and general construction of the storage means 168 is identical to that of the storage means 68 hereinabove described, except for the extended neck portion 183 connecting with gate section 172. Gate section 172 is also identical in general function and construction to gate section 72 hereinabove described.

In operation, tubing portion 48' is anchored and positioned on mold core 56 in a manner identical to that previously described for the injection molding embodiment, and the remaining length 48 is inserted through neck 183 and coiled for storage in the cavity in storage means 168. Then the mold core 56 will be dipped sucessively in a source of liquid plastic material 109 to apply successive coats 108 of the material on the mold core 56 until the desired thickness is achieved. The plastic material will also coat a portion of the neck 183 and gate section 172, but that material may be easily trimmed from the prosthesis at the gate 172 interface at 45 with the prosthesis body (see FIG. 1).

FIGS. 11A and 11B show a prosthesis 120 that is formed in a combination of injection molding and dip molding steps. In FIG. 11A a prosthesis 120 is shown partially completed after having been injection molded to imbed tubing 48' in wall portion 134. However, the prosthesis terminates in an open end having a shoulder 136. In the next step, the injection molded prosthesis of FIG. 11A is then dip-molded in accordance with the process and apparatus of FIG. 10, to provide an overall thin layer 134' of molded material bonded to but overlying the injection molded body 134.

By extending the dip-molded portion beyond the end 136, a thin, sleeve-like portion 138 will be formed that corresponds to the thin, sleeve-like portion 38 as shown in FIG. 1, while the resulting shoulder 136' corresponds to the annular ridge or shoulder 36 as shown in FIG. 1. Of course, the storage means, 68 and 168 as hereinbefore described, can be utilized in protecting the excess tubing 48 during each of the injection molding and the dip molding steps in accordance with this invention.

Numerous variations and modifications may be made in the structure herein described without departing from the present invention. Accordingly, it should be clearly understood that the forms of the invention herein described and shown in the figures of the accompanying drawings are illustrative only and are not intended to limit the scope of the invention.

I claim:

1. Apparatus for molding a product from a thermo plastic or thermosetting material in which the product has integrally embedded therein a portion of a pre-formed non-rigid elongated member, the remaining length and free end of the pre-formed non-rigid member extending from the molded product to form an elongated appendage projecting therefrom, comprising:

a mold for forming the product from the selected material, means for anchoring one end of the preformed member at a selected position on said mold, a portion of the pre-formed member succeeding said anchored one end being positioned along at least a portion of the mold surface, storage means mounted on said mold and cooperating therewith for storing and protecting the remaining length and free end of the pre-formed non-rigid member exending past a predetermined exit location in the surface of the molded product during the molding process, and means for applying the selected molding material to said mold for forming the product and integrally imbedding said portion of the pre-formed non-rigid member within the molded product, said protected remaining length and free end of the pre-formed member when removed from said storage means forming an elongated appendage projecting from the molded product.

2. The apparatus of claim 1, wherein said storage means comprises:

a box-like member having a storage cavity disposed therein and constructed of a material suitable for protecting the pre-formed non-rigid member during the molding process, said box-like member mounted on said mold for cooperating therewith, said box-like member having a gate section therein for accepting and protecting the remaining length and free end of the pre-formed member extending past said molded product surface exit location and cooperating with said mold for defining at least a portion of the surface of the molded product, said box-like member further having a channel disposed in at least a portion of one face thereof and communicating with said storage cavity and said gate section to direct the remaining length and free end of said pre-formed member into said cavity for storage, and lid means adopted to sealingly cover said box-like member including said channel disposed therein.

3. The apparatus of claim 2, wherein said gate section comprises:

defined outer surfaces along one side of said box-like member cooperating with said mold surfaces for defining at least a portion of the surface of the molded product and said predetermined exit location for the pre-formed member from the molded product surface, and said defined outer surface having an aperture therethrough for sealingly accepting the remaining length of the pre-formed member.

4. Apparatus for molding a product from a thermoplastic or thermosetting material in which the product has integrally imbedded therein a portion of a non-rigid elongated member, the remaining length and free end of the pre-formed member extending from the molded product to form an elongated appendage projecting therefrom, comprising:

a mandrel carrying a mold core, means for anchoring one end of the pre-formed member at a selected position on said mold core, a first portion of the pre-formed member succeeding said anchored one end being positioned along at least a portion of the surface of said mold core, storage means mounted on said mandrel and positionable closely adjacent said mold core for storing and protecting the remaining length and free end of the preformed member extending past a predetermined exit location from the surface of the molded product, said means further storing and protecting said remaining length and free end of the pre-formed member during the molding process, a pair of female mold halves having a cavity therein for cooperatively mating with said mold core to form a product mold cavity, at least one of said female mold halves having disposed in a mating face thereof a box-like recess for receiving and carrying said storage means mounted on said mandrel during the molding process, and means for injecting the liquid molding material into said product mold cavity to form the molded product and integrally imbedding said first portion of the pre-formed member therein, said remaining length and free end of the pre-formed member when removed from said isolation and storage means forming an elongated appendage projecting from the molded product.

5. The apparatus of claim 4, wherein said storage means comprises:

a box-like member having a storage cavity therein and constructed of a material suitable for protecting the pre-formed non-rigid member during the molding process and adopted for mounting on said mandrel for being movably positionable adjacent said mold core, said box-like member including a gate section therein positionable adjacent said mold core surface for accepting the remaining length and free end of the pre-formed member extending past said predetermined exit location from the surface of the molded product, said gate section further having defined outer surfaces cooperating with said mold core surface and said product mold cavity for defining at least a portion of the surface of the molded product and the exit location of the pre-formed member therefrom, said box-like member further having a channel disposed in at lease a portion of the face thereof for accomodating a portion of the remaining length of the pre-formed member therein and communicating between said cavity and said defined outer surfaces of said gate section, means for mounting said box-like member on said mandrel for permitting limited arcuate movement of said box-like mandrel and mold core for permitting said defined outer surfaces of said gate section to be moved into and out of a closely spaced relationship with said mold core surface, and lid means adapted to cover and seal said box-like member including said channel disposed therein.

6. The apparatus of claim 5, wherein said gate section includes and defined surfaces along one side of said box-like member and an aperature therethrough communicating with said channel in said box-like member, said aperature adapted for sealingly accepting and isolating the remaining length of the pre-formed member extending therethrough.

7. The apparatus of claim 6, wherein said gate section further includes an elongated lip projecting from said body member on one side of said channel adjacent said aperature and partially closing said channel adjacent said aperature for frictionally engaging said pre-formed member.

8. The apparatus of claim 7, wherein said lid means includes a flat lid member shaped to conform to the configuration of said box-like member and said gate section and frictionally sealing therewith, said lid member having a grooved cavity therein registering with the longitudinal space remaining between the extending end of said lip and the other side of said channel.

9. The apparatus of claim 6, further including a flat washer-shaped member disposed concentrically about said pre-formed member adjacent said gate section aperature for cooperating therewith to improve the seal between said pre-formed member and said aperature to prevent intrusion of the molding material into said box-like member channel.

10. The apparatus of claim 5, wherein said means for mounting said box-like member comprises:
a mounting lug extending from said box-like member and having a transverse aperature therethrough,
a slot disposed in the side of a portion of said mandrel for cooperatively accepting said lug, and
a pin disposed transversely through said mandrel slot and engaging said lug aperature for permitting rotational movement of said lug with respect thereto.

11. Apparatus for injection molding a generally cylindrical sleeve-like penile prosthesis from a thermoplastic or thermosetting material utilizing a male mold core and a pair of female mold halves in which the molded prosthesis has integrally imbedded in a wall therein a portion of a pre-formed length of resilient tubing, the remaining length and free end of the tubing extending from the molded prosthesis as a length of free tubing projecting therefrom, comprising:
a mandrel carrying the male mold core and adapting for mounting between the female mold halves,
means for anchoring one end of the preformed tubing at a selected position on the mold core,
a first portion of the tubing after said anchored one end being positioned adjacent at least a portion of the mold core,
isolation and storage means mounted on said mandrel and positionable adjacent the mold core surface for accepting and isolating the remaining length and free end of the tubing extending past a predetermined location for the tubing to exit the molded prosthesis, said means further storing and protecting said isolated remaining length and free end of the tubing during the injection molding process,
at least one of the female mold halves having disposed in a mating face thereof a box-like recess for receiving and carrying said isolation and storage means mounted on said mandrel during the molding process, and
means for injecting a liquid molding material into said female mold halves for molding the prosthesis and integrally imbedding said first portion of the tubing within the wall of the prosthesis,
said remaining length and free end of the tubing when removed from said isolating and storage means forming a length of free tubing projecting from the molded prosthesis.

12. The apparatus of claim 11, wherein said isolation and storage means comprises:
a box-like member having a storage cavity disposed therein and constructed of a material resistant to the temperature and pressure of the injection molding process and adapted for mounting on said mandrel adjacent said mold core for cooperating therewith,
said box-like member including a gate section positionable adjacent the mold core surface for accepting and isolating the remaining length of the tubing extending past said pre-determined exit location from the prosthesis, said gate section further having defined surfaces cooperating with said mold core and female mold half surfaces for defining at least a portion of the surface of the prosthesis and the exit location of the tubing from the molded product,
said box-like member further having a channel disposed in at least a portion of the face thereof and communicating between said cavity and said gate section defined surfaces for accommodating a portion of the remaining length of the tubing therein,
means for mounting said box-like member on said mandrel for permitting limited arcuate movement of said box-like member with respect to said mandrel and mold core and permitting said defined surfaces of said gate section to be moved into and out of a closely spaced relationship with said mold core surface, and
lid means adapted to cover and seal said box-like member including said channel disposed therein for protecting the remaining length and free end of the tubing.

13. The apparatus of claim 12, wherein said means for mounting said box-like member comprises:
a mounting lug extending from said box-like member and having a transverse aperature therethrough,
a slot disposed in the side of a portion of said mandrel for cooperatively accepting said mounting lug, and
a pin disposed transversely through said mandrel slot and engaging said lug aperature for permitting rotational movement of said lug with respect thereto.

14. The apparatus of claim 12, wherein said gate section includes said defined surfaces of said box-like member and an aperature therethrough communicating with said channel in said boxlike member, said aperature adapted for sealingly accepting and isolating the remaining length of the tubing extending therethrough.

15. The apparatus of claim 14, wherein said gate section further includes an elongated lip projecting from said body member on one side of said channel adjacent said aperature and partially closing said channel adjacent said aperature for frictionally engaging and compressing the tubing.

16. The aperature of claim 15, wherein said lid means includes a flat lid member shaped to conform to the configuration of said box-like member and said gate section and frictionally sealing therewith, said lid member having a grooved cavity therein registering with the longitudinal space remaining between the extending end of said lip and the other side of said channel for accommodating any portion of the resilient tubing protruding therethrough.

17. The apparatus of claim 14, further including a flat washer-shaped member disposed concentrially about the tubing adjacent said gate section aperature for cooperating therewith to improve the seal between the tubing and said aperature to prevent extrusion of the molding material into said box-like member channel.

18. The apparatus of claim 3, wherein said mold further includes a pair of female mold halves having a cavity defined therein for forming a product mold cavity, and wherein at least one of said female mold halves has a box-like recess for receiving and carrying said storage means mounted on said mandrel during the molding process.

19. The apparatus of claim 3, wherein said mold comprises a mold core carried by a mandrel, and wherein said storage means is mounted on said mandrel and said mold core is utilized for applying successive layers of dip-molded layers of the liquid molding material over the mold core to form the molded product.

* * * * *